(12) United States Patent
Baldwin

(10) Patent No.: US 10,124,127 B2
(45) Date of Patent: Nov. 13, 2018

(54) WEARABLE WRIST INHALER

(71) Applicant: Kendra Baldwin, Windsor Mill, MD (US)

(72) Inventor: Kendra Baldwin, Windsor Mill, MD (US)

(*) Notice: Subject to any disclaimer, the term of this patent is extended or adjusted under 35 U.S.C. 154(b) by 0 days.

(21) Appl. No.: 15/384,632

(22) Filed: Dec. 20, 2016

(65) Prior Publication Data

US 2017/0100551 A1 Apr. 13, 2017

Related U.S. Application Data

(63) Continuation-in-part of application No. 14/880,915, filed on Oct. 12, 2015, now Pat. No. 9,550,032.

(60) Provisional application No. 62/062,953, filed on Oct. 12, 2014.

(51) Int. Cl.
*A61M 11/04* (2006.01)
*A61M 11/08* (2006.01)
*A61M 15/00* (2006.01)

(52) U.S. Cl.
CPC ........ *A61M 15/0025* (2014.02); *A61M 11/04* (2013.01); *A61M 11/08* (2013.01); *A61M 15/008* (2014.02); *A61M 15/009* (2013.01); *A61M 15/0021* (2014.02); *A61M 15/0043* (2014.02); *A61M 15/0051* (2014.02); *A61M 15/0055* (2014.02); *A61M 2202/064* (2013.01); *A61M 2205/8206* (2013.01); *A61M 2209/088* (2013.01)

(58) Field of Classification Search
CPC ...... A61M 11/00; A61M 11/04; A61M 11/06; A61M 11/08; A61M 15/00; A61M 15/009
See application file for complete search history.

(56) References Cited

U.S. PATENT DOCUMENTS

| | | | | |
|---|---|---|---|---|
| 5,855,307 A * | 1/1999 | Biddick | ............... | A45F 5/00 128/205.22 |
| 6,223,744 B1 * | 5/2001 | Garon | ............... | A61M 15/00 128/200.14 |
| 6,557,737 B1 * | 5/2003 | Hanson | ............... | A45F 5/00 128/200.14 |
| 7,156,092 B2 * | 1/2007 | Otter | ............... | B63C 11/22 128/201.18 |
| 2007/0119450 A1 * | 5/2007 | Wharton | ............... | A61M 15/00 128/200.23 |
| 2007/0125372 A1 * | 6/2007 | Chen | ............... | A61M 15/0065 128/200.23 |

(Continued)

*Primary Examiner* — Michael Tsai
(74) *Attorney, Agent, or Firm* — Dale J. Ream

(57) ABSTRACT

A wearable wrist inhaler includes a wristband having a first end and a second end configured for wear about a user's wrist. An inhaler unit is removably coupled to the wristband displaced from the first end and the second end, the inhaler unit including a housing having a plurality of walls defining an interior area and an outlet port in communication with the interior area. A watch assembly is positioned atop the housing of the inhaler unit, the watch assembly energized by a battery and includes a display configured to indicate a time of day. A dosage chamber including a medicament is positioned in the interior area of the housing. A dispensing assembly is communication with the inhaler medicament that is configured to dispense an individual portion of the medicament via the outlet port upon demand by a user.

9 Claims, 23 Drawing Sheets

(56) References Cited

U.S. PATENT DOCUMENTS

2010/0083963 A1\* 4/2010 Wharton .................. A45F 5/00
128/203.15

\* cited by examiner

WEARABLE WRIST INHALER

REFERENCE TO RELATED APPLICATIONS

This application claims the benefit of non-provisional patent application Ser. No. 14/880,915 filed Oct. 12, 2015 titled Wearable Wrist Inhaler which claims the benefit of provisional patent application U.S. Ser. No. 62/062,953 filed Oct. 12, 2014 titled Wrist Inhaler, both of which are incorporated herein by reference.

BACKGROUND OF THE INVENTION

The present invention relates generally to the field of inhaler devices and more specifically relates to a specially designed wearable asthma inhaler configured in the form of a wristwatch to provide fast effective relief of asthma symptoms, as an ordinary inhaler would, while remaining readily accessible on the user at all times.

A metered-dose inhaler (MDI) is a device that delivers a specific amount of medication to the lungs, in the form of a short burst of aerosolized medicine that is usually self-administered by the patient via inhalation. It is the most commonly used delivery system for treating asthma, chronic obstructive pulmonary disease (COPD) and other respiratory diseases. The medication in a metered dose inhaler is most commonly a bronchodilator, corticosteroid or a combination of both for the treatment of asthma and COPD. Other medications less commonly used but also administered by MDI are mast cell stabilizers, such as cromoglicate or nedocromil.

Various attempts have been made to solve problems found in inhaler device art. Among these are found in: U.S. Pat. No. 5,855,307 to Biddick et al; U.S. Pub. No. 2006/0032495 to Jennifer Fernandez; and U.S. Pub. No. 2002/0130149 to Kimberly Howell. This prior art is representative of body-mountable inhaler devices.

None of the above inventions and patents, taken either singly or in combination, is seen to describe the invention as claimed. Thus, a need exists for a reliable Wearable Wrist Inhaler, a specially designed wearable asthma inhaler configured in the form of a wristwatch to provide fast effective relief of asthma symptoms, as an ordinary inhaler would, while remaining readily accessible on the user at all times and to avoid the above-mentioned problems.

SUMMARY OF THE INVENTION

In view of the foregoing disadvantages inherent in the known inhaler device art, the present invention provides a novel wrist inhaler. The general purpose of the present invention, which will be described subsequently in greater detail, is to provide a specially designed wearable asthma inhaler configured in the form of a wristwatch to provide fast effective relief of asthma symptoms, as an ordinary inhaler would, while remaining readily accessible on the user at all times. The features of the invention which are believed to be novel are particularly pointed out and distinctly claimed in the concluding portion of the specification. These and other features, aspects, and advantages of the present invention will become better understood with reference to the following drawings and detailed description.

The wrist inhaler includes a specially designed waterproof unit. The wrist inhaler would be worn like any other watch, and would be made available in a plethora of variations, colors and styles to appeal to individual tastes. As such, various versions may be produced including a sports version, casual, child's version, business professional versions, and more. The wrist inhaler may be sized appropriately for wear by adults and children.

In addition to displaying the time and date, the wrist inhaler includes a specially designed and sized inhaler unit discreetly integrated into the watch body, which can be easily refilled with medication as necessary. In an embodiment, a handy angle adjustable mouth piece with protective cap covering protrudes slightly from the unit to enable the user to inhale the medication. Across from this mouth piece is the actual pump dispenser. This dispenser would be capped as well to ensure medicine is not accidentally discharged. Featuring a sturdy and comfortable adjustable band, the wrist inhaler may be an unobtrusive and stylish device. The streamline watch face would feature an actual working watch face featuring a digital or analog display. This display would reveal the time, date, and approximate number of puffs remaining. As the medicine is refilled, the "puffs remaining" indicator could be reset.

The wrist inhaler allows those living with asthma the freedom to go anywhere with their rescue inhaler conveniently attached and ever present. Fashioned from waterproof materials, the wrist inhaler could easily go from land to water without worry, as well as be exposed to the elements without compromising the unit. As such, users could rest assured that whichever activity they are participating in could be done without preoccupation of whether or not the unit was near, or that it may be destroyed by weather or activity.

Simply stated, the wrist inhaler could mean the difference between a small attack and a full blown asthma attack. It could also mean the difference between life and death when seconds matter. Ever ready with a quick shake of the wrist, the wrist inhaler would deliver asthma medication quickly and efficiently, without the need to track down the inhaler, wasting precious time. In addition, with one's inhaler conveniently attached, one would not have to worry about anyone tampering with their life saving unit. Cleverly conceived and thoughtfully designed, the wrist inhaler is an innovative and ever ready life saving concept for those living with asthma. The wrist inhaler is cost-effective to produce in the embodiments, as shown in the figures.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

Therefore, a general object of this invention is to provide a wrist inhaler that is wearable on the wrist of a person and enables a dose of bronchial medicament to be available at the press of a button.

Another object of this invention is to provide a wearable wrist inhaler, as aforesaid, that includes an inhaler unit coupled to a working wristwatch.

Still another object of this invention is to provide a wearable wrist inhaler, as aforesaid, having an adjustable mouthpiece so that an inhaled dose may be dispensed without removing the inhaler from a user's wrist.

Yet another object of this invention is to provide a wearable wrist inhaler, as aforesaid, that is refillable.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2b is a sectional view taken along line 2b-2b of FIG. 2a;

FIG. 4b is a sectional view taken along line 4b-4b of FIG. 4a;

FIG. 5b is a sectional view taken along line 5b-5b of FIG. 5a;

FIG. 6b is a sectional view taken along line 6b-6b of FIG. 6a;

FIG. 7b is a sectional view taken along line 7b-7b of FIG. 7a;

FIG. 15b is a sectional view taken along line 15b-15b of FIG. 15a; and

FIG. 16a is an exploded view of the wrist inhaler as in FIG. 15a.

DESCRIPTION OF THE PREFERRED EMBODIMENT

Figure 1:
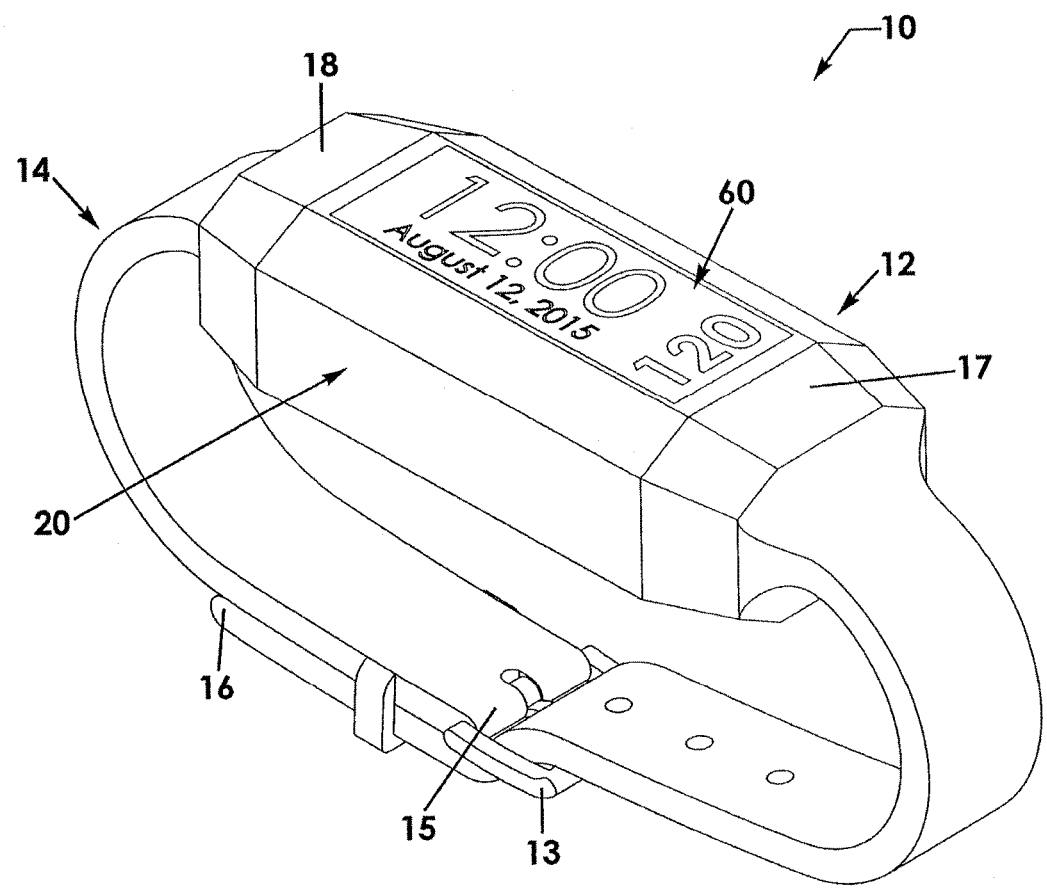
FIG. 1 is a perspective view of a wearable wrist inhaler according to one embodiment of the present invention.
Figure 2A:
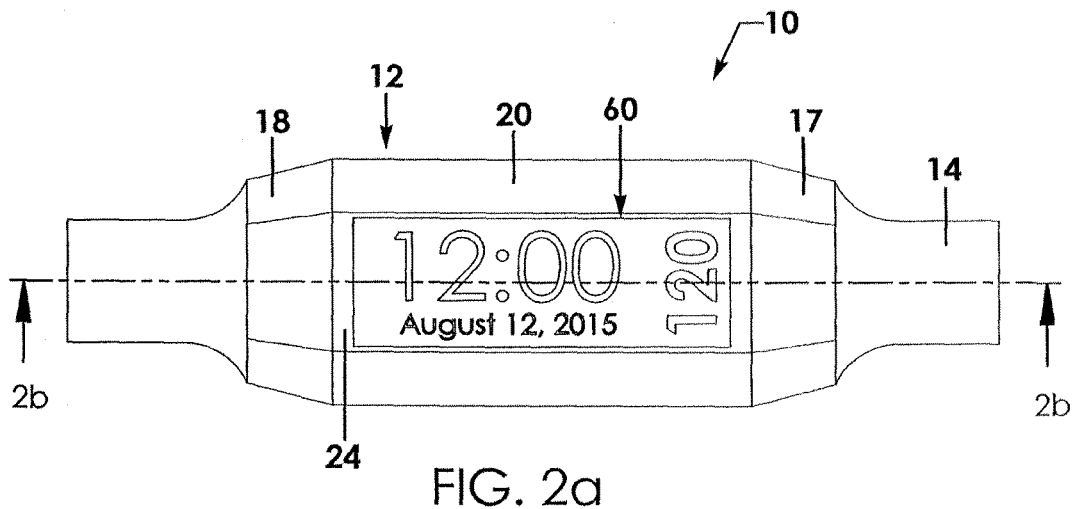
FIG. 2a is a top view of the wrist inhaler as in FIG. 1.
Figure 2B:
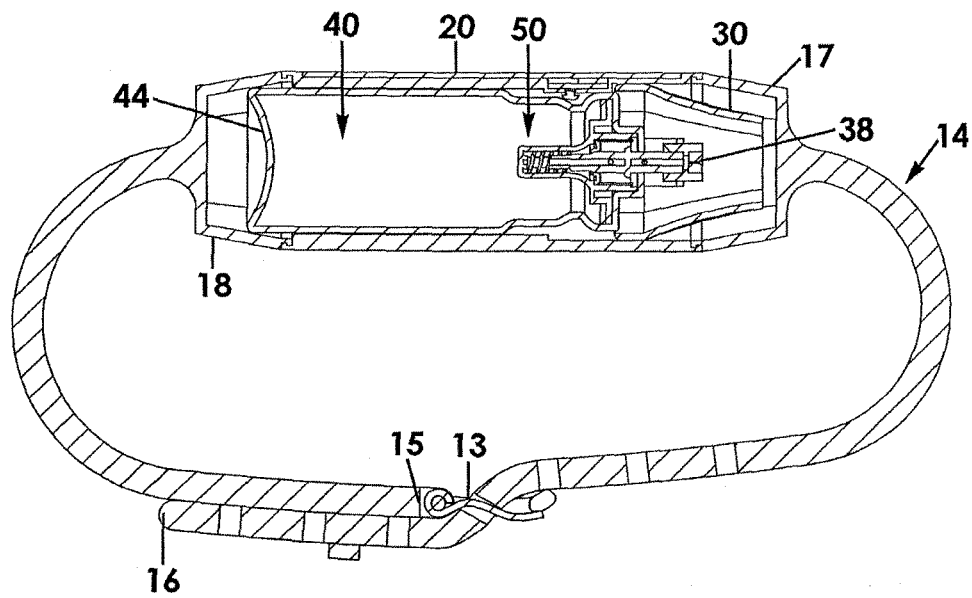

A wearable wrist inhaler according to a preferred embodiment of the present invention will now be described with reference to FIGS. 1 to 16a of the accompanying drawings. In an embodiment, the wearable wrist inhaler 10 includes a wristband 14 and a pump type inhaler unit 12 situated between opposed ends of the wristband 14 and having a digital watch assembly 60 and display 62. In another embodiment, a gear-driven inhaler unit 102 is situated between opposed ends of the wristband 114 and includes a watch assembly 60'.

Figure 3:
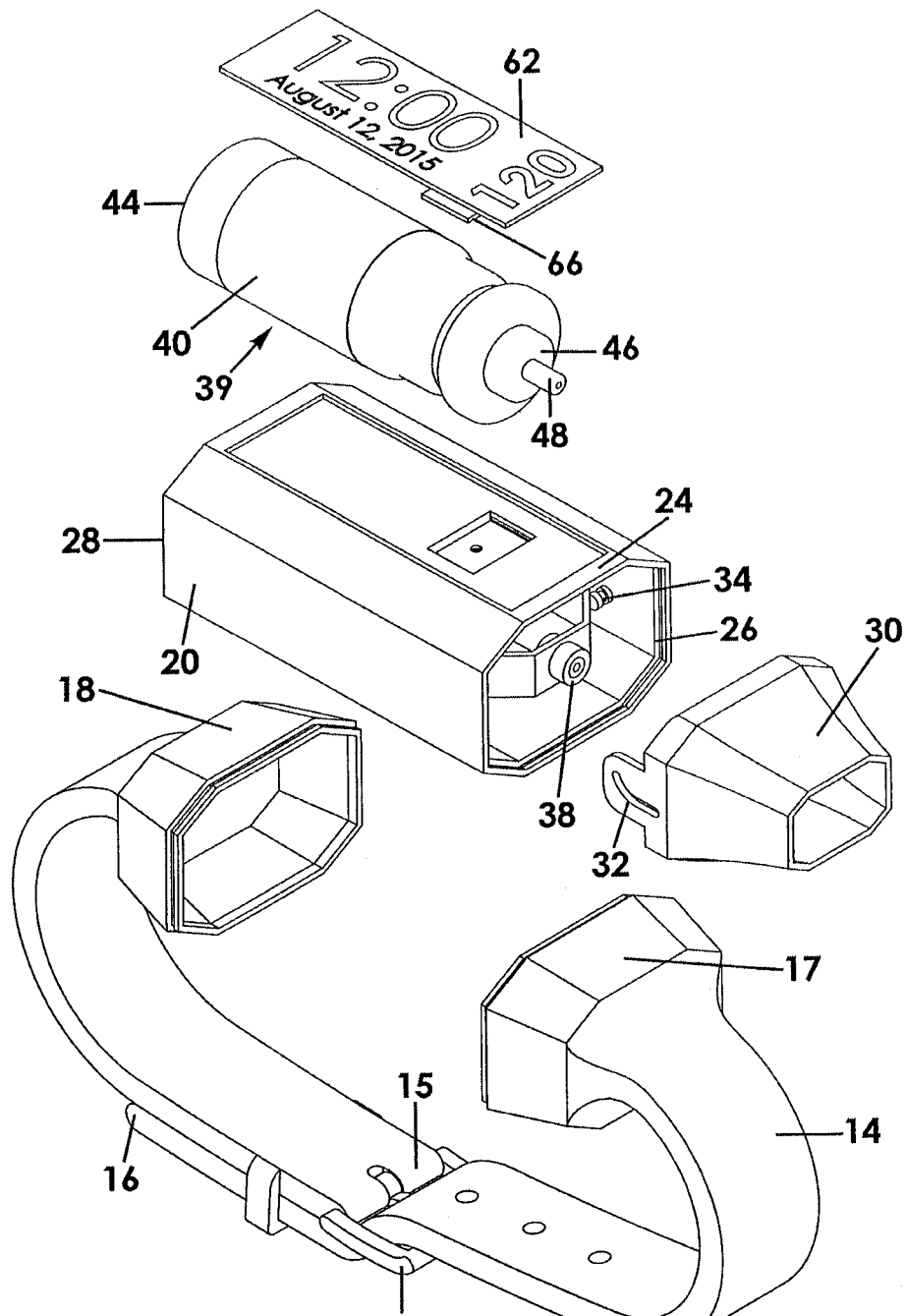
FIG. 3 is an exploded view of the wrist inhaler as in FIG. 1.
Figure 4A:
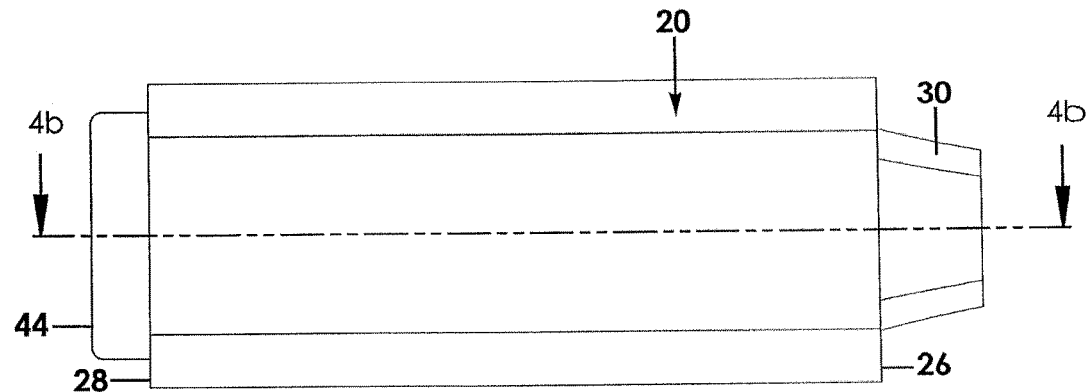
FIG. 4a is a side view of the inhaler unit as in FIG. 1.
Figure 4B:
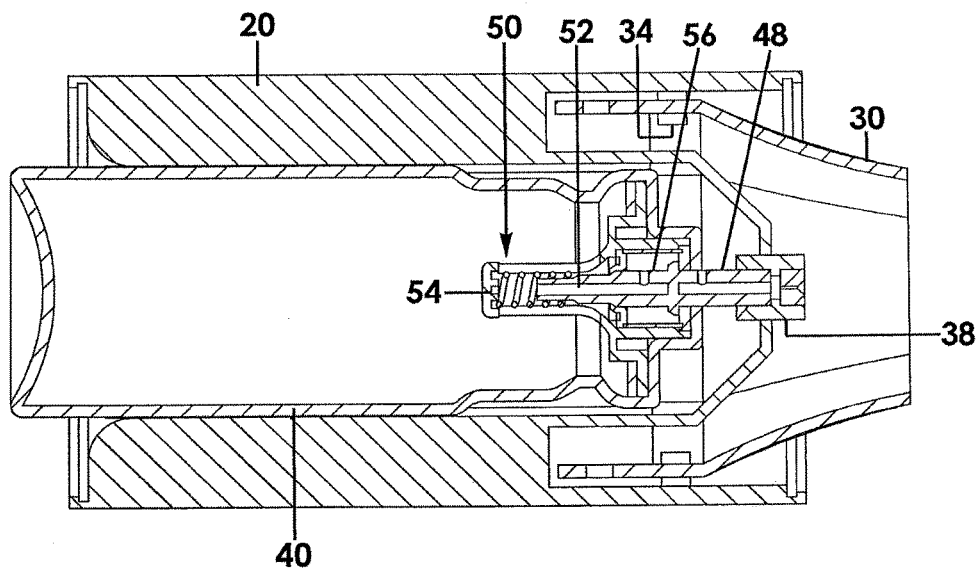

As shown in FIGS. 1 to 7, the wristband 14 includes a first end 15 and a second end 16 that may be selectively fastened together, such as with a buckle 13 or similar fastener, such that the wristband 14 is configured so as to be wearable about a user's wrist. The wristband 14 includes a first cap member 17 and a second cap member 18. In an embodiment, the pump type inhaler unit 12 is releasably coupled between the first cap member 17 and second cap member 18, such as by a friction or snap fit attachment (FIG. 3). It is understood that the inhaler unit 12 is only operable when released from the first cap member 17 and second cap member 18.

The inhaler unit 12 includes a housing 20 having a bottom wall 22, an opposed top wall 24, and respective side walls extending between top and bottom walls. Collectively, the walls define an interior area, an open front end 26 and a rear end 28. The front and rear ends provide access into the interior area.

Figure 5A:
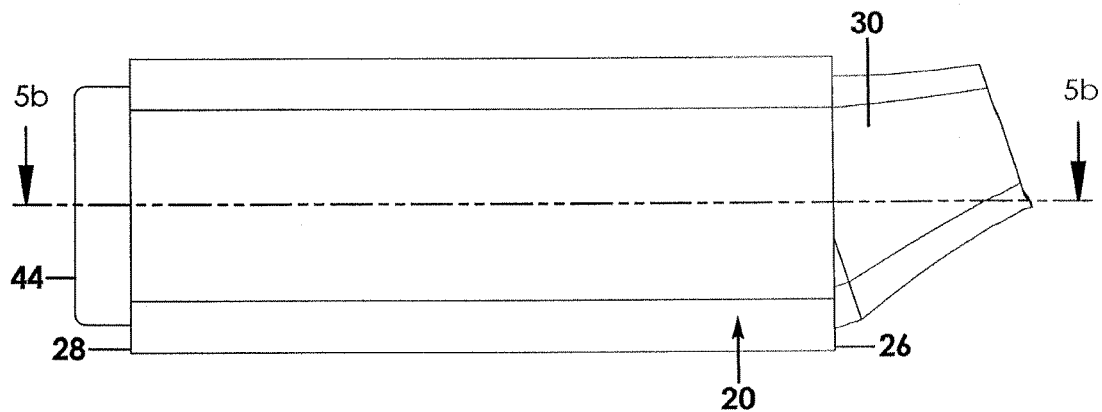
FIG. 5a is a side view of the inhaler unit as in FIG. 4a, illustrating the mouthpiece in a pivoted configuration.
Figure 5B:
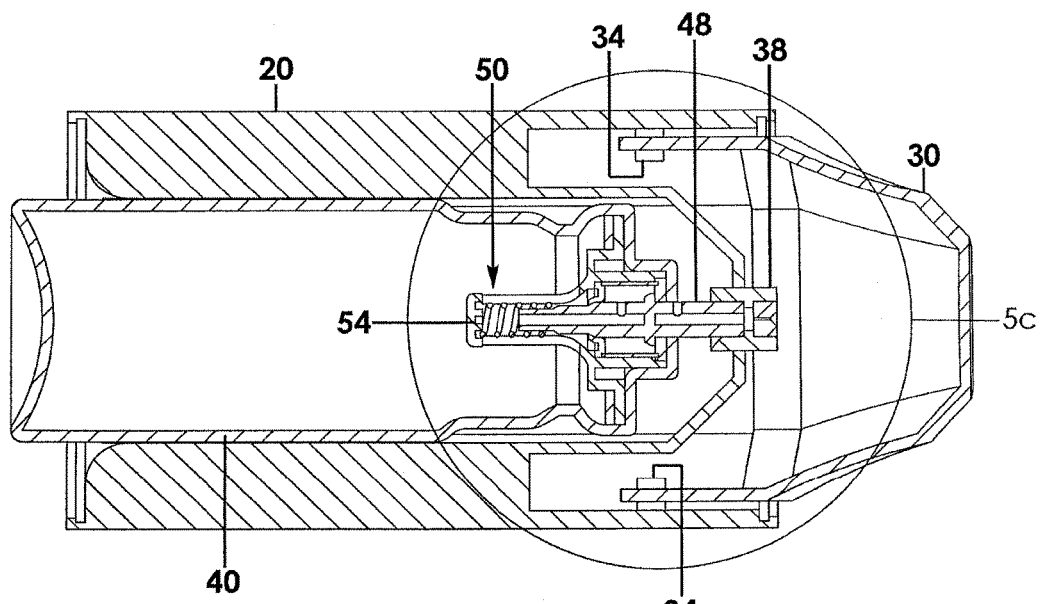
Figure 5C:
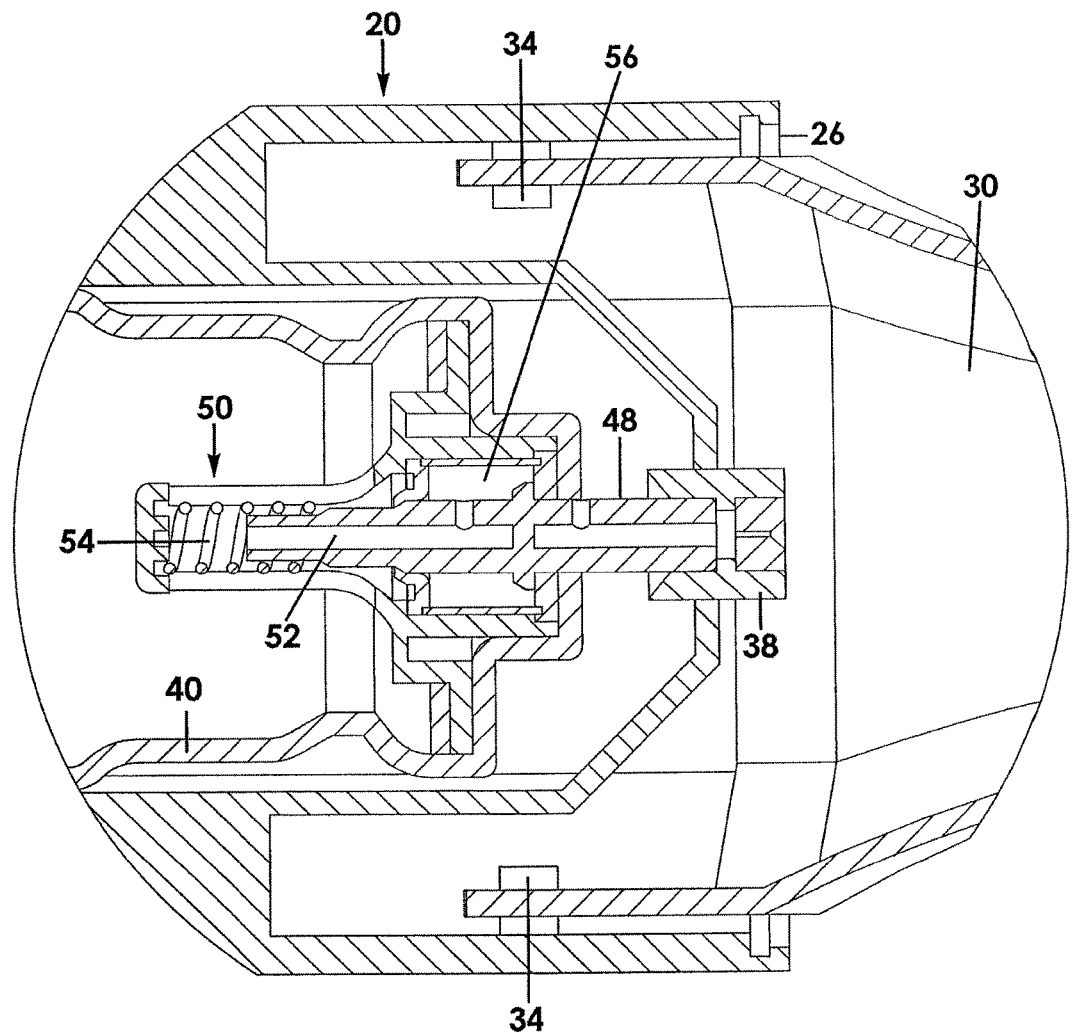
FIG. 5c is an isolated view on an enlarged scale taken from FIG. 5b, illustrating the spring and dispenser assembly in a relaxed or normal configuration.
Figure 5D:
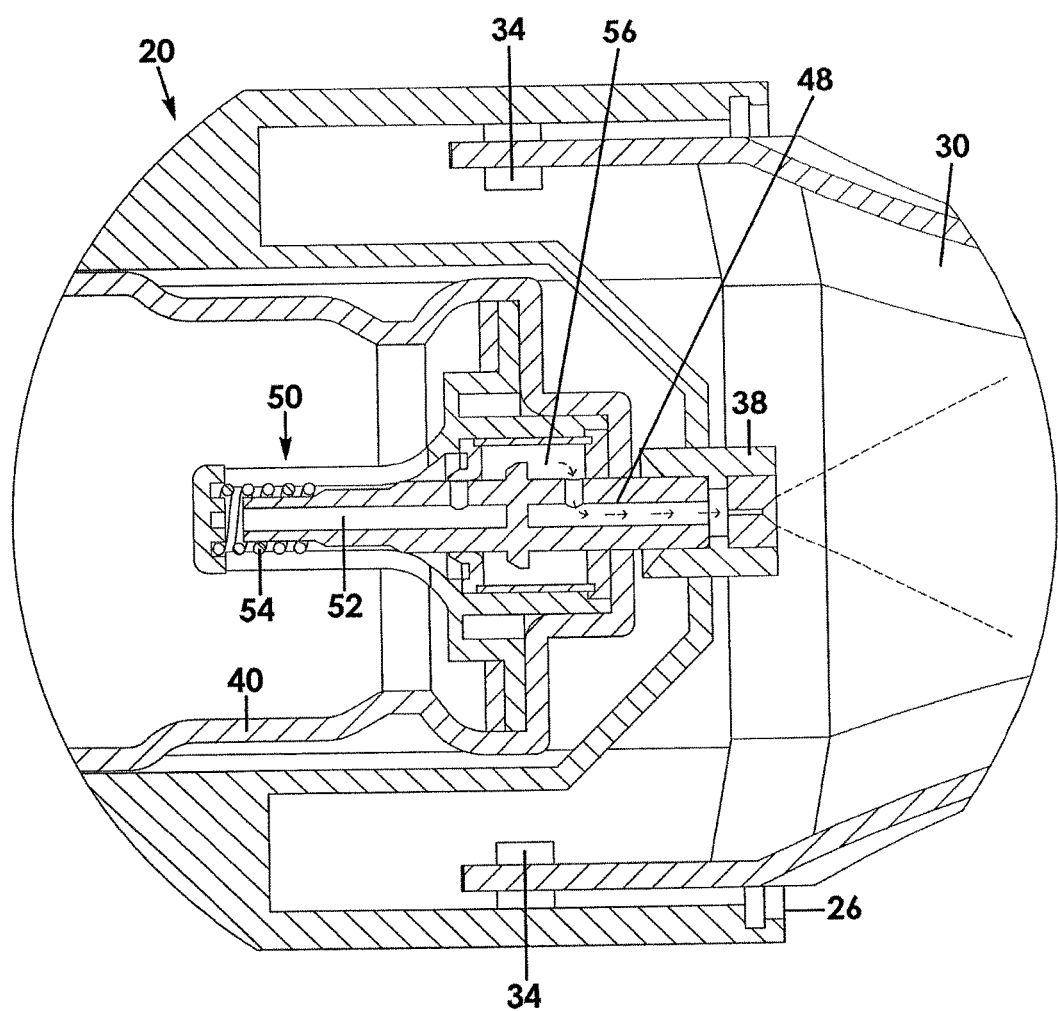
FIG. 5d is an isolated view on an enlarged scale taken from FIG. 5b, illustrating the spring and dispenser assembly in a compressed or actuated configuration.
Figure 6A:
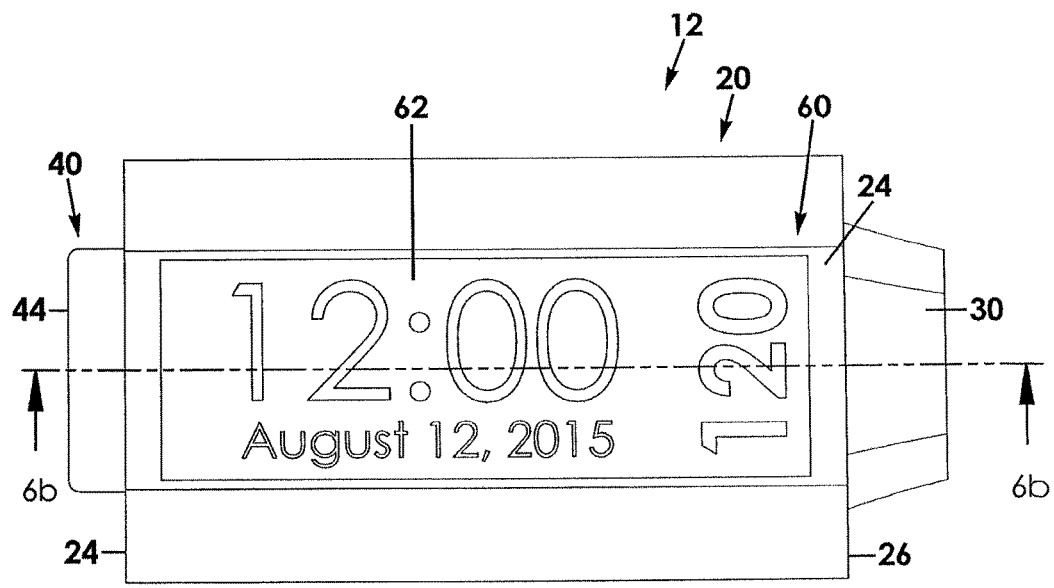
FIG. 6a is a top view of the inhaler unit as in FIG. 1.
Figure 6B:
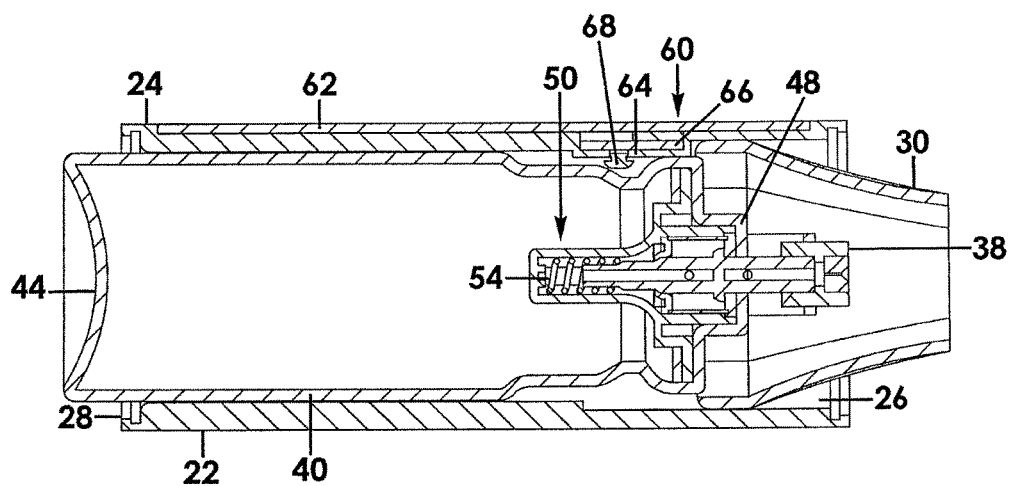

A mouthpiece 30 is pivotally coupled to the housing 20 and situated adjacent the front end 26 and configured to have its angle selectively moved by a user. Specifically, the mouthpiece 30 may include a pair of mounting brackets each defining a guide slot 32 having a generally arcuate configuration (FIGS. 3 and 5c). Correspondingly, the a pair of guide posts 34 may be mounted to inner surfaces of the housing 20 to which respective guide slots 32 are mounted. The guide slots 32 are slidable along respective guide posts 34 so that the mouthpiece may be pivotally moved to desired angles relative to the housing 20. The open front end 26 of the housing 20 may also be referred to as an outlet port.

The inhaler unit 12 includes a medicine canister 40 containing a plurality of individual doses of a medicament that may be dispensed via the outlet port 128 on demand by a user. In an embodiment, the dispensing assembly 36 includes an actuator nozzle 38 mounted in said interior area of the housing 20 adjacent the open front end 26. The medicine canister 40 situated in the interior area that includes a distal end 44 accessible through the open rear end 28 of the housing 20 and an opposed proximal end 46 adjacent the actuator nozzle 38. The medicine canister 40 includes a canister reservoir 42 configured to hold a liquid medicine, e.g. for the treatment of an asthma attack. It is understood that the medicine canister 40 is removable from the housing 20, such as to be replaced when the canister reservoir 42 is empty.

Further, the medicine canister 40 includes a valve stem 48 situated at the proximal end 46. The valve stem 48 is configured to be received or nested in the actuator nozzle 38 when the medicine canister 40 is inserted into the interior area of the housing 20. The valve stem 48 is operatively in fluid communication with the canister reservoir 42. More particularly, medicine canister 40 includes an actuator assembly 50 coupled to the valve stem 48 and defining a channel 52 between the canister reservoir 42 and the valve stem 48 and configured to deliver doses of medicine.

Figure 7A:
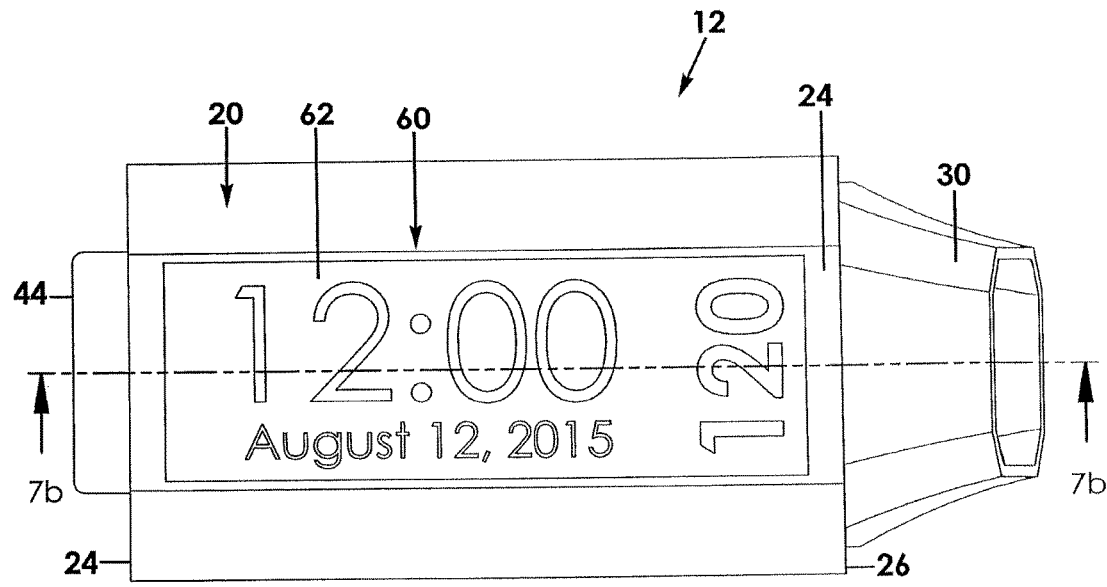
FIG. 7a is another top view of the inhaler unit as in FIG. 1 illustrating the mouthpiece in a pivoted configuration.
Figure 7B:
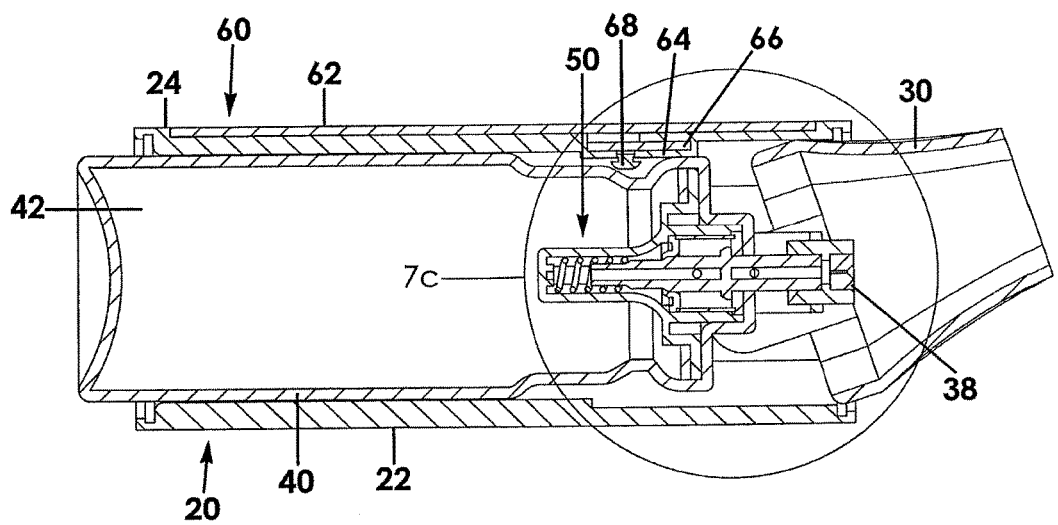
Figure 7C:
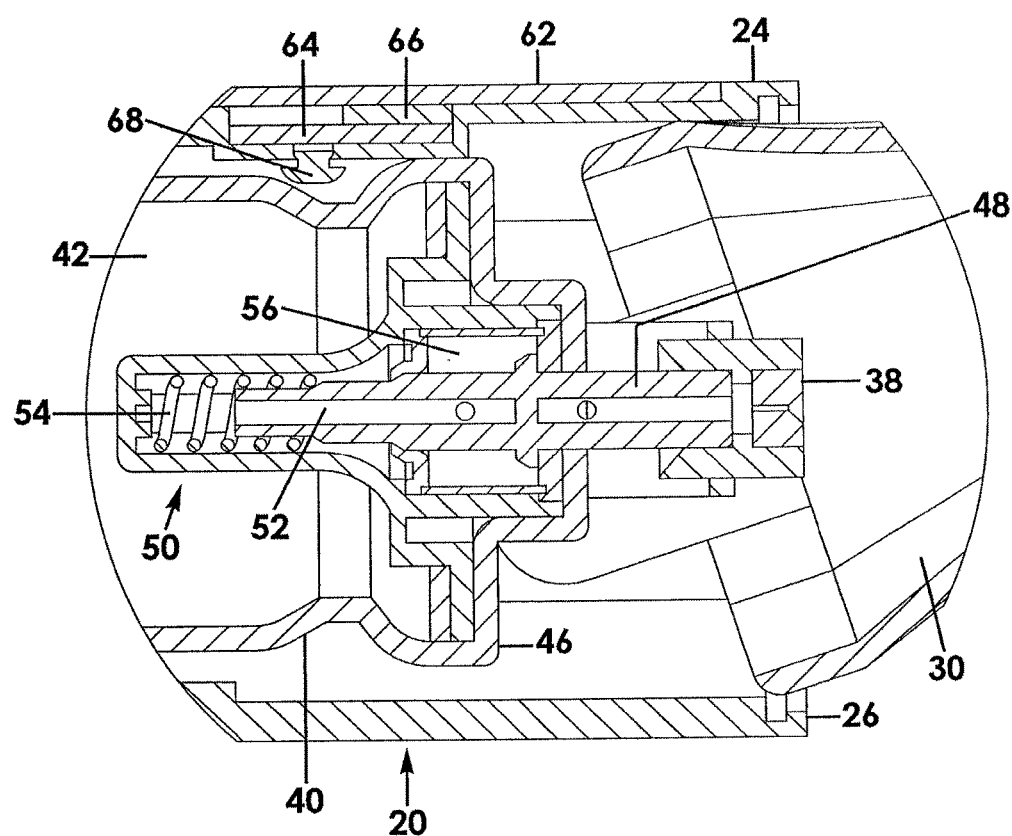
FIG. 7c is an isolated view on an enlarged scale taken from FIG. 7c, illustrated with the spring and dispensing assembly in a relaxed configuration.

The actuator assembly 50 is movable between a relaxed configuration and a deployed configuration. The channel 52 is configured such that medicine from the canister reservoir 42 is blocked from flowing from the canister reservoir 42 to the valve stem 48 when the actuator assembly 50 is at a relaxed configuration and medicine from the canister reservoir 42 is allow to flow from the canister reservoir 42 to the valve stem 48 when the actuator assembly 50 is at a deployed (depressed) configuration. More particularly, the actuator assembly 50 includes a compression spring 54 that normally biases the actuator assembly 50 away from the actuator nozzle 38 and toward the relaxed configuration (FIGS. 5c and 7c). By contrast, the actuator assembly 50 may be pressed or pushed to the deployed configuration (FIGS. 5d and 7d) at which the spring 54 is compressed.

A user may manually urge the medicine canister 40 further into the interior area of the housing 20 and the actuator assembly 50 to the deployed configuration. In doing so, the valve stem 48 is firmly pressed into engagement with the actuator nozzle 38 and the spring 54 is compressed, allowing medicine to flow through the channel 52 to the valve stem 48 and out the actuator nozzle 38.

Considering the dispensing of medicine even further, the channel 52 is in fluid communication with a dosage chamber 56 formed in the actuator assembly 50. When the actuator assembly 50 is at the relaxed configuration, medicine is allowed to flow into the dosage chamber 56 via the channel 52 (FIG. 5c). Accordingly, a predetermined dosage of medicine is prepared for later dispensing. Then, when the actuator assembly 50 is moved to the deployed configuration, the predetermined amount of medicine is allowed to flow from the dosage chamber 56 into the valve stem 48 (FIG. 5d) where it is dispensed through the actuator nozzle 38 and mouthpiece 30 as described above.

The watch assembly 60 includes a digital display 62 positioned atop the top wall 24 of the housing 20. A circuit board 64, traditional circuitry, or a processor may be positioned in the housing 20 and electrically connected for data communication with the digital display 62. The circuit board 64 is configured to keep time and to display it on the digital display. A battery 66 is electrically connected to the circuit board 64 so as to energize it and the digital display 62.

Figure 7D:
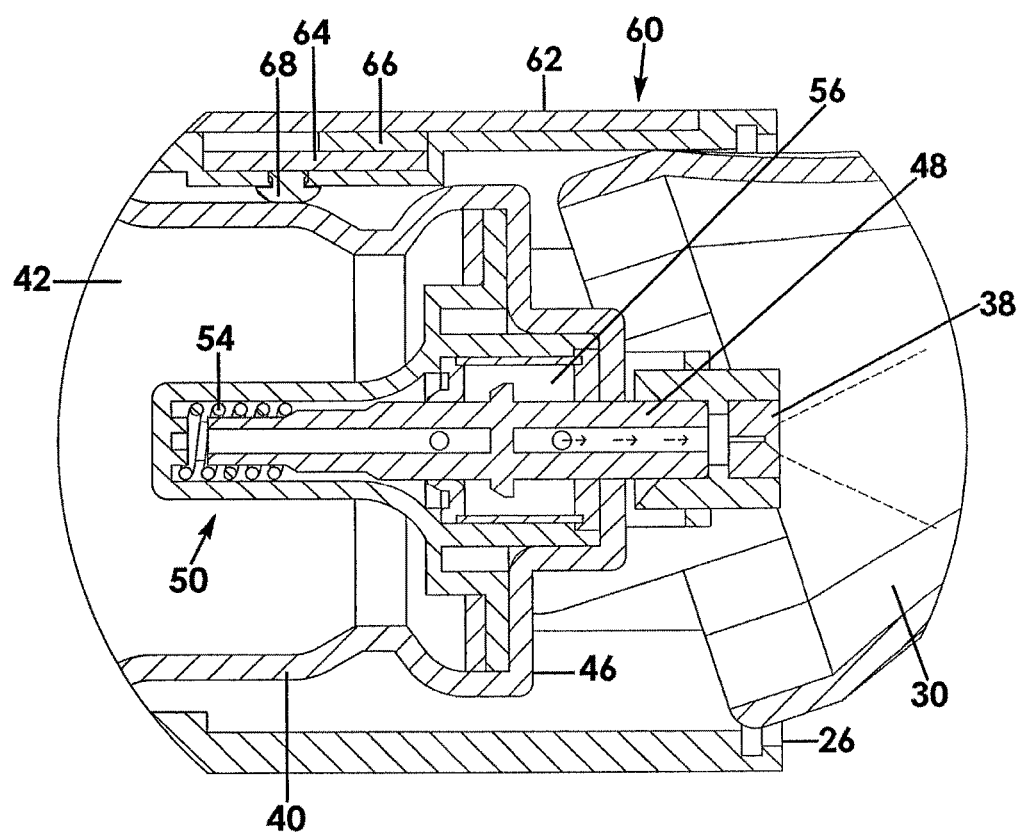
FIG. 7d is an isolated view on an enlarged scale taken from FIG. 7c, illustrated with the spring and dispensing assembly in a compressed or actuated configuration.
Figure 8A:
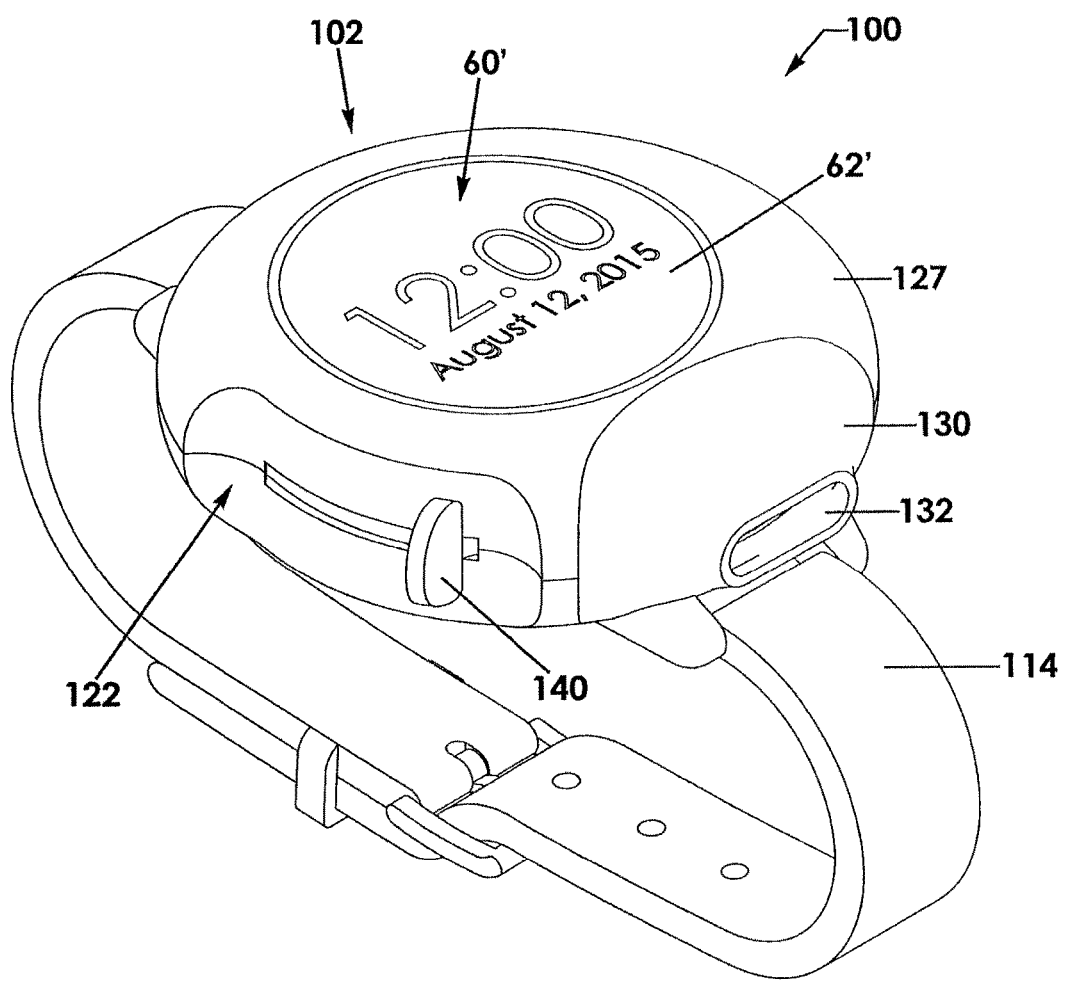
FIG. 8a is a perspective view of a wearable wrist inhaler according to another embodiment of the present invention.
Figure 8B:
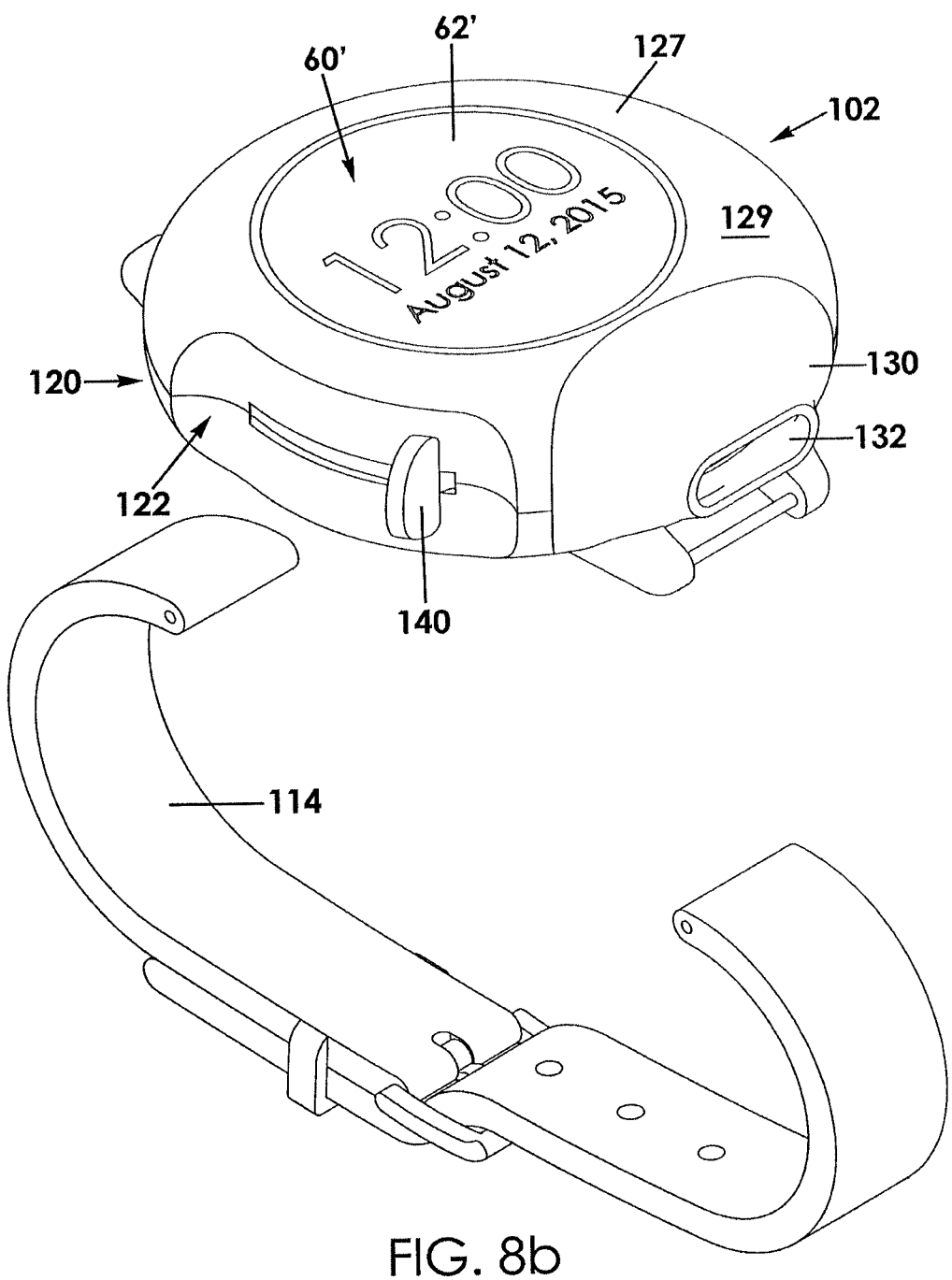
FIG. 8b is an exploded view of the wrist inhaler as in FIG. 8a, illustrating the inhaler unit separated from a wrist band.

In addition, the watch assembly 60 may include a digital dosage counter 68 for calculating the number of doses of medicine that have been dispensed by inhaler unit 12 and displaying that number on the digital display 62. The dosage counter 68 may be an electromechanical component coupled directly to the circuit board 64. Preferably, the dosage counter 68 extends into the interior area of the housing 20 such that it is contacted and pressed each time the medicine canister 40 is pushed to the deployed configuration (FIG. 7d).

In use, the inhaler unit 12 may be released from the wristband 14 and actuated to dispense a single dose of an asthma medication stored in a medicine canister 40. Specifically, the medicine canister 40 may be pushed deeper into the housing 20 and into firm engagement with the actuator nozzle 38 until the spring 54 is compressed and medicine flows from a dosage chamber 56 into the valve stem 48 and through the actuator nozzle 38 and mouthpiece 30.

In related embodiment specifically illustrated in FIGS. 14a to 16a of the accompanying drawings, the housing 20 is removably coupled to the wristband 14 in a uniquely defined manner. In this embodiment, the mouthpiece 30 includes a strap fastener 31 configured to be removably coupled to a corresponding fastener on the wristband. In other words, the strap fastener 31 of the mouthpiece 30 is removably coupled to the wristband 14. This strap fastener 31 is also present in the embodiment described below and was recited in the claims of the related (parent) application referenced above, now patented.

Another embodiment of the present invention is shown in FIGS. 8a-13 and will be described below. In this embodiment of a wearable wrist inhaler 100, an inhaler unit 102 may be a gear-driven type of dispenser of doses of medicine packaged an elongate medicine strip 104, the medicine strip 104 having a first layer 106 and a second layer 108.

Now more particularly, the wrist inhaler 100 includes a housing 120 having a base portion 122 and a lid portion 127 removably coupled to the base portion 122. The housing 120 presents a generally circular configuration. The base portion 122 includes a bottom wall 124 and a side wall 126 extending upwardly from a peripheral edge of the bottom wall 124. Together, the bottom wall 124 and side wall 126 define an interior area in which other components are situated as will be described below. The housing 120 may be coupled to a wrist band 114.

The lid portion 127 includes a top wall 129 configured to cover or enclose the interior area of the base portion 122 when coupled thereto. The side wall 126 of the base portion 122 defines an outlet port 128. A mouthpiece 130 may be coupled to the wrist inhaler housing 120 adjacent to the outlet port 128, the mouthpiece 130 defining an open distal end 132 such that medicine dispensed through the outlet port 128 may also be transmitted through the mouthpiece 130 to a user's mouth. Receipt of the medicine is enhanced, of course, by an inhalation by a user's mouth on the mouthpiece 130.

Figure 9A:
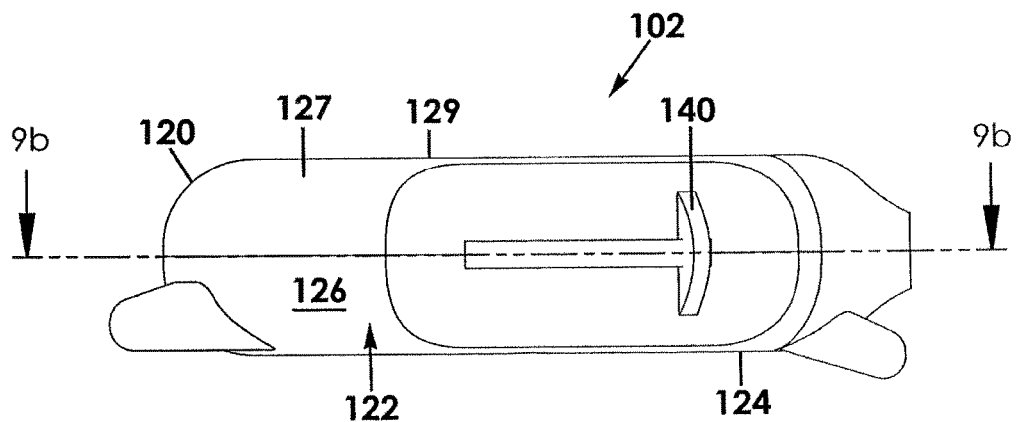
FIG. 9a is a side view of the inhaler unit as in FIG. 8b.
Figure 9B:
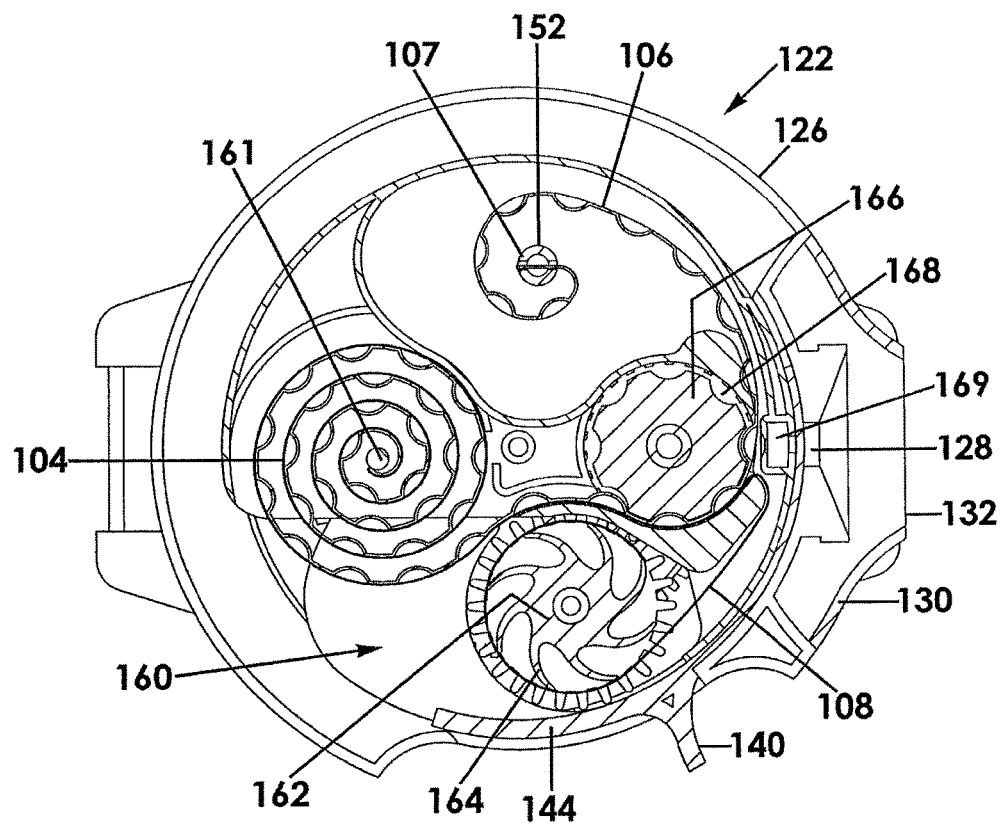
FIG. 9b is a sectional view taken along line 9b-9b of FIG. 9a, illustrating the lever in an unactuated or relaxed configuration.
Figure 9C:
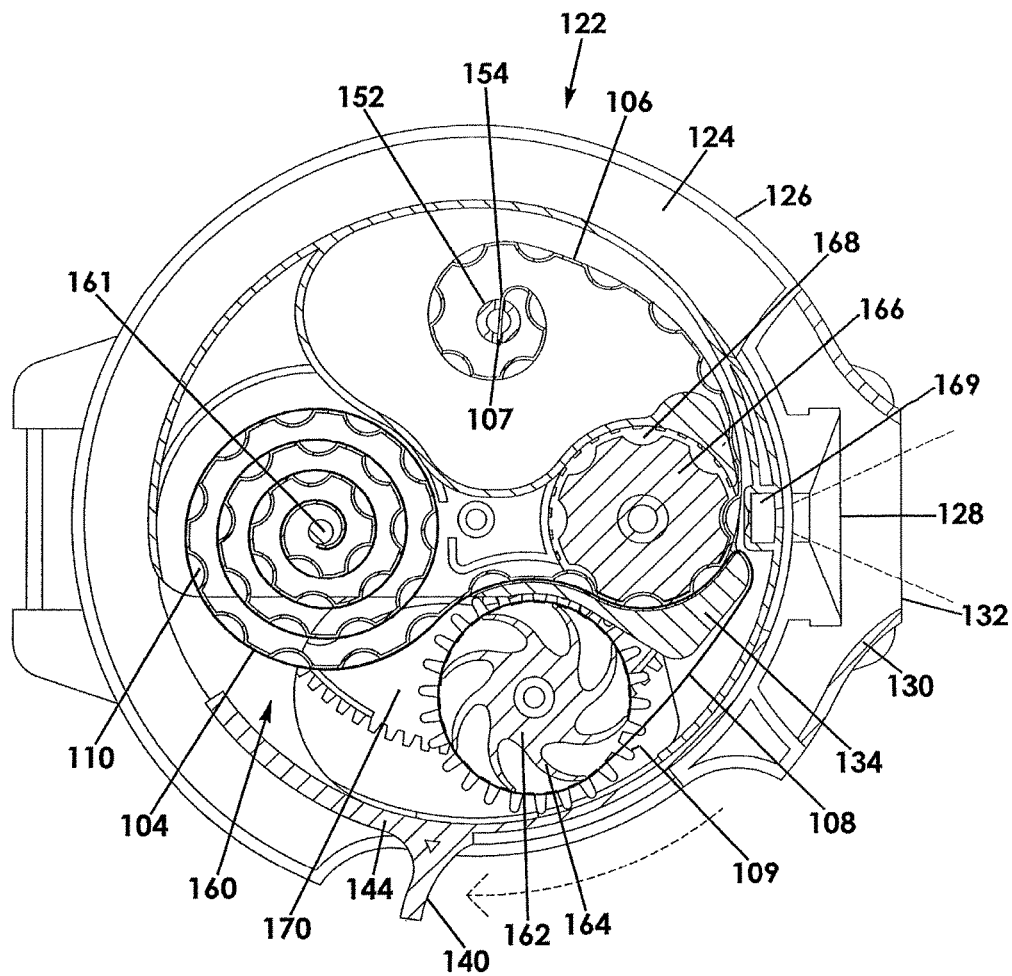
FIG. 9c is a sectional view taken along line 9b-9b of FIG. 9a, illustrating the lever in an actuated or deployed configuration.

The dispensing assembly 160 of the present embodiment of the wrist inhaler 100 includes a medicine container having an upstanding post 161 about which the elongate medicine strip 104 is coiled (FIG. 9c). Further, the dispensing assembly 160 includes a contracting wheel 162 rotatably mounted to the bottom wall 124 of the base portion 122 of the housing 120. In an embodiment, the contracting wheel 162 has a plurality of fins 164 configured to engage the medicine strip 104 so as to pull the medicine strip 104 from its coiled position about the post 161 when the contracting wheel 162 is rotated. An index wheel 166 is rotatably mounted in the base portion 122 of the housing 120 and operatively coupled to the contracting wheel 162, the index wheel 166 defining a plurality of spaced apart pockets 168 or cutouts configured to selectively receive individual portions 110 of medicine from the medicine strip 104 as the medicine strip 104 is uncoiled from the upstanding post 161 and passed across the index wheel 166.

The dispensing assembly 160 may include a dosage chamber 169 adjacent the outlet port 128. The dosage chamber 169 is configured and positioned in the base portion 122 to receive a respective individual portion of medicine when the medicine strip 104 is pulled apart into the first layer 106 and second layer 108 as will be described later. The respective individual portion of medicine is preferably a powder.

A lever 140 is operatively coupled to the contracting wheel 162 and to the index wheel 166 such that respective wheels are rotated upon a slidable movement of the lever 140. The lever 140 is positioned and configured to extend away from the side wall 126 of the base portion 122 and is movable by a manipulative action of a user. The lever 140 is slidably movable between actuated and unactuated configurations.

Figure 10A:
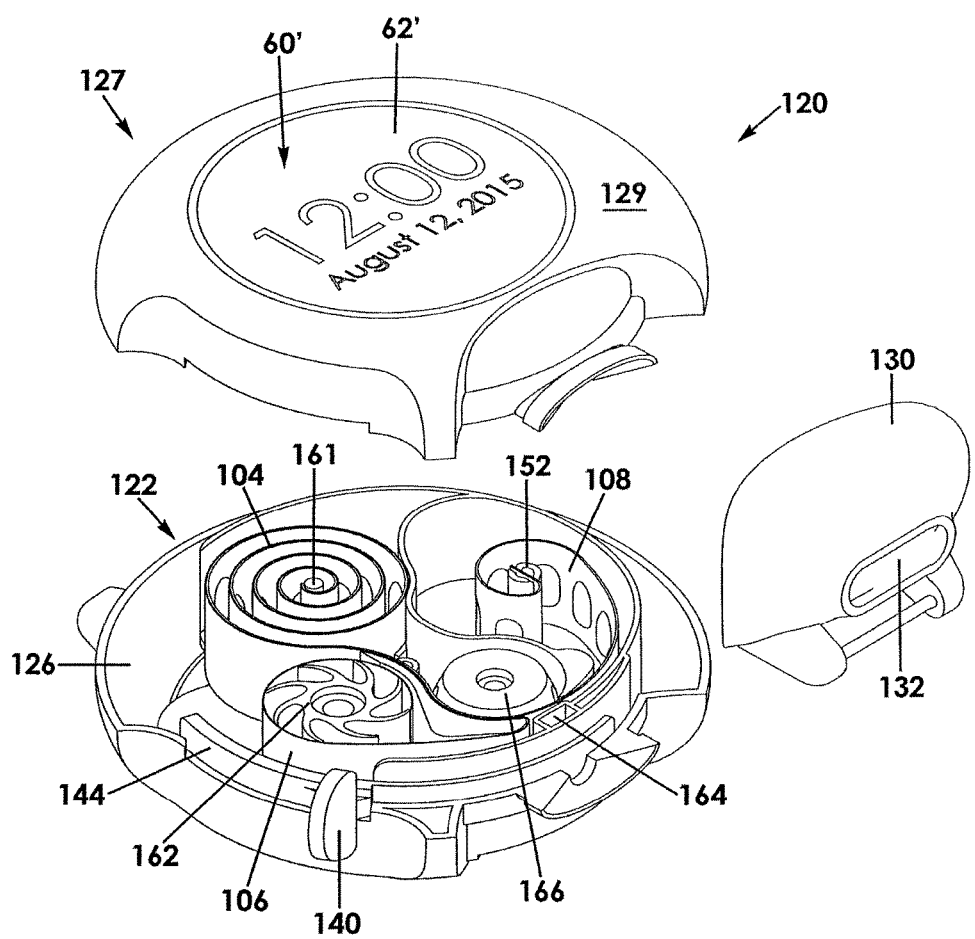
FIG. 10a is an exploded view of the housing as in FIG. 9b.
Figure 10B:
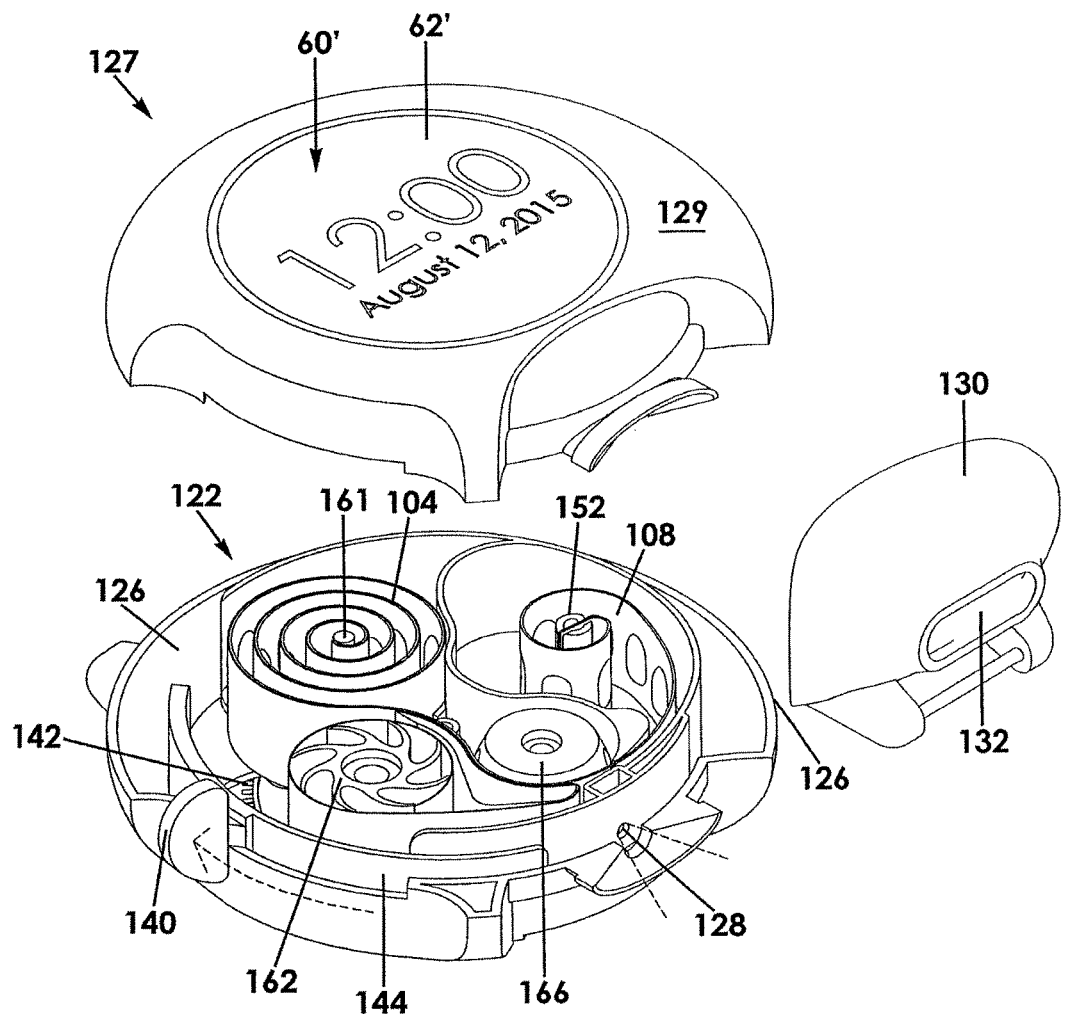
FIG. 10b is an exploded view of the housing as in FIG. 9c.
Figure 11:
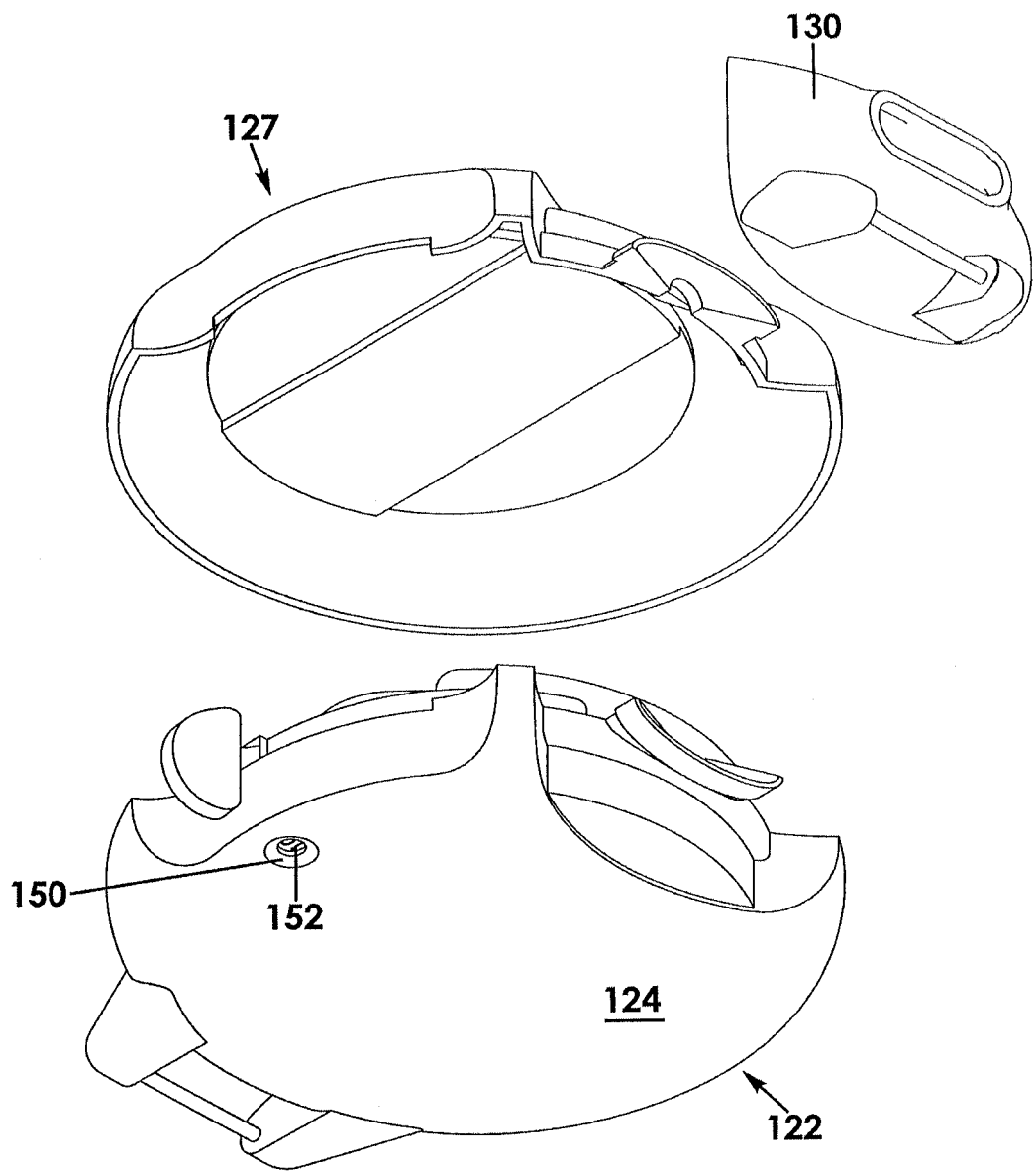
FIG. 11 is a bottom perspective view of the inhaler unit as in FIG. 10b.
Figure 12:
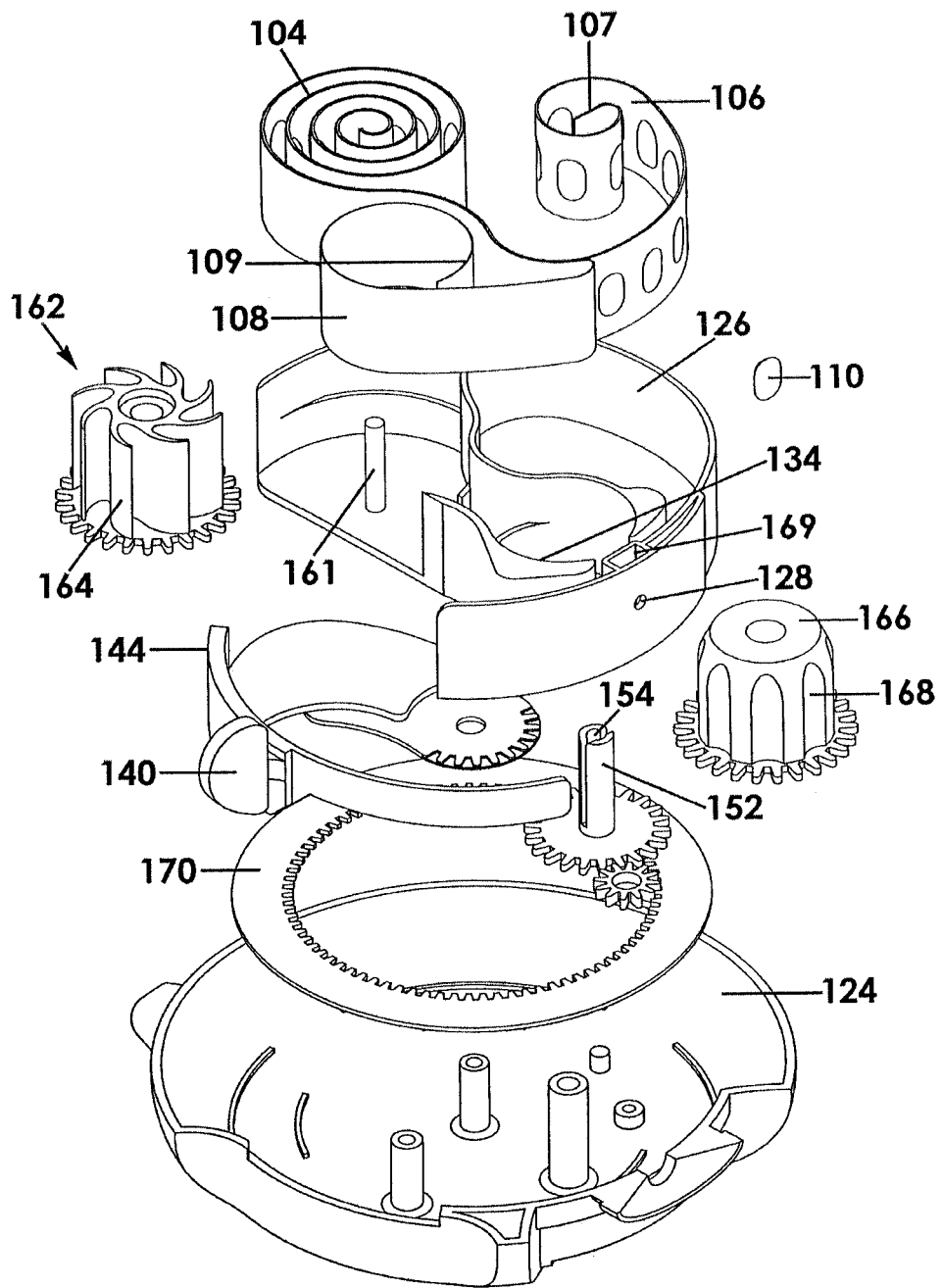
FIG. 12 is an exploded view of the base portion of the housing.
Figure 13:
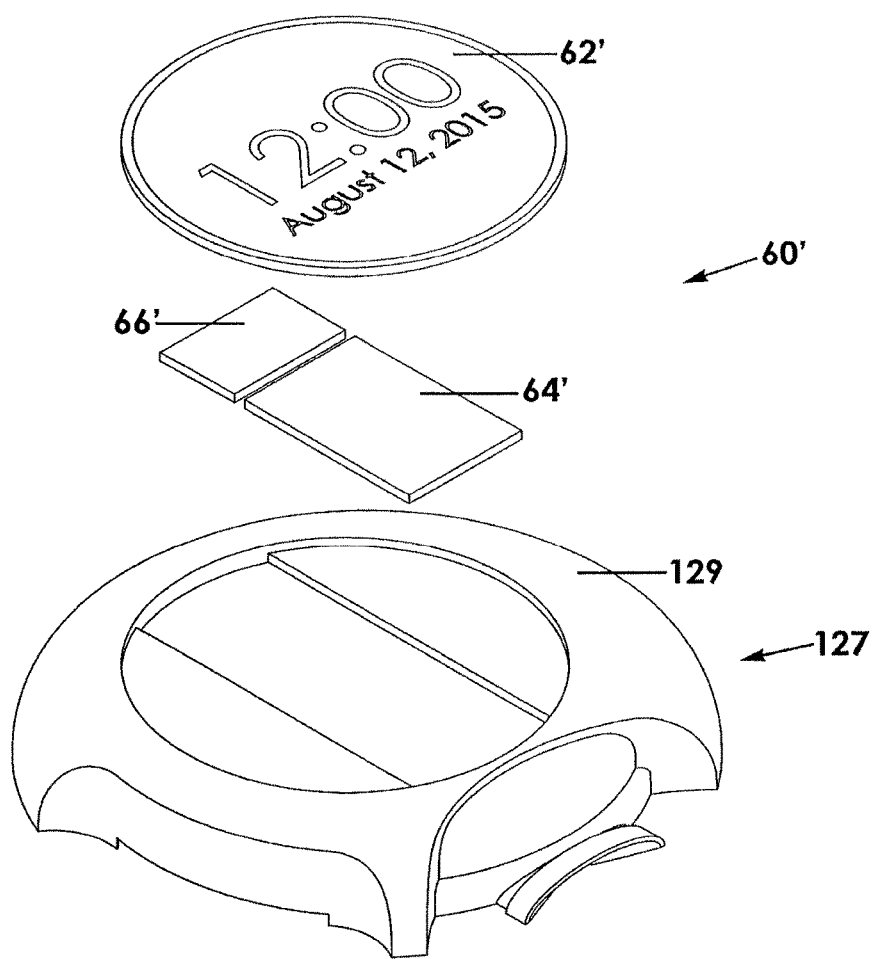
FIG. 13 is an exploded view of the watch assembly and lid portion of the housing.
Figure 14A:
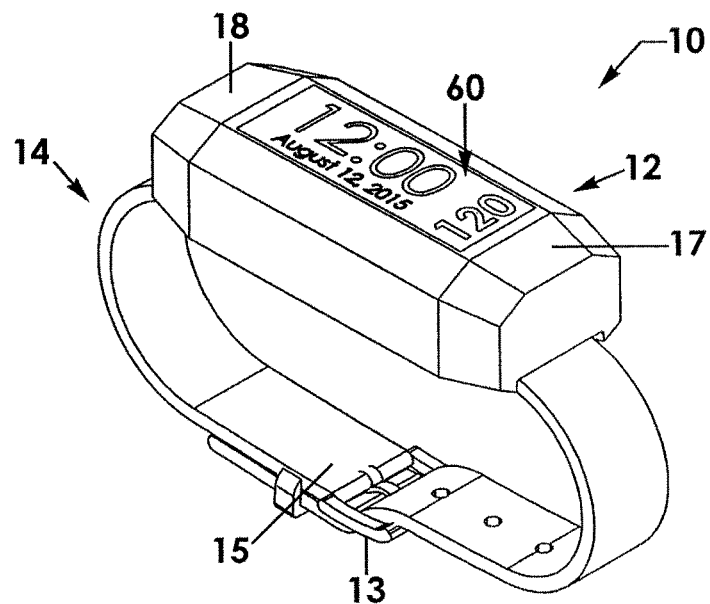
FIG. 14a is a perspective view of a wearable wrist inhaler according to another embodiment of the present invention.
Figure 14B:
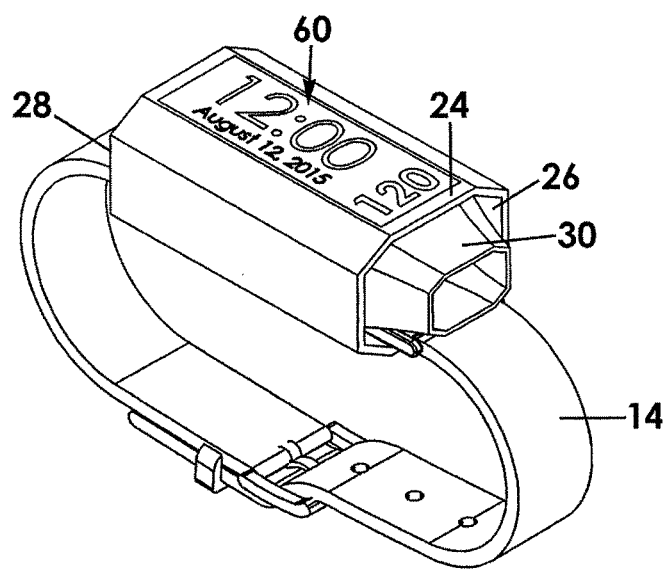
FIG. 14b is a perspective view of the wrist inhaler as in FIG. 14a with the protective end caps removed for clarity.
Figure 15A:
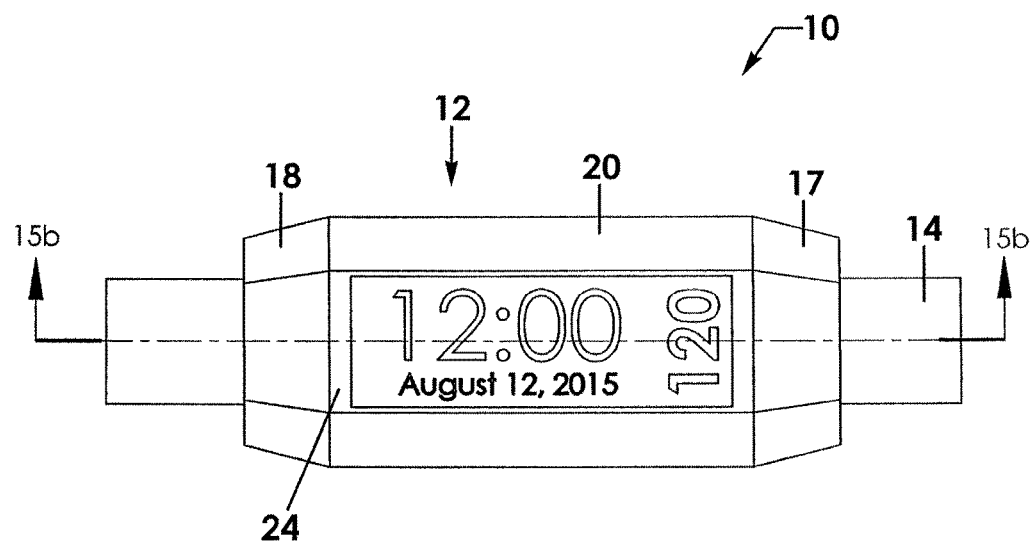
FIG. 15a is a top view of the wrist inhaler as in FIG. 14b.
Figure 15B:
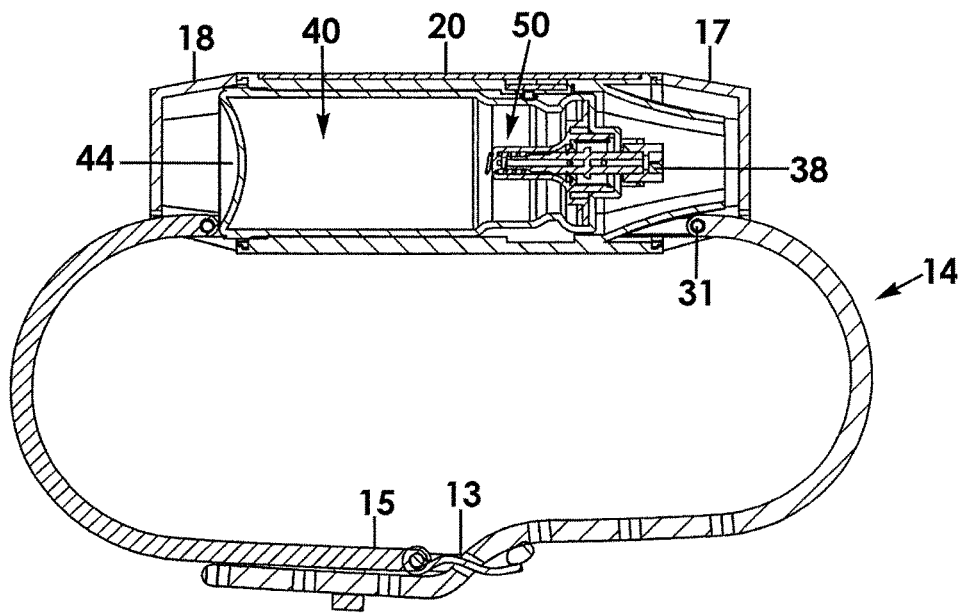
Figure 16A:
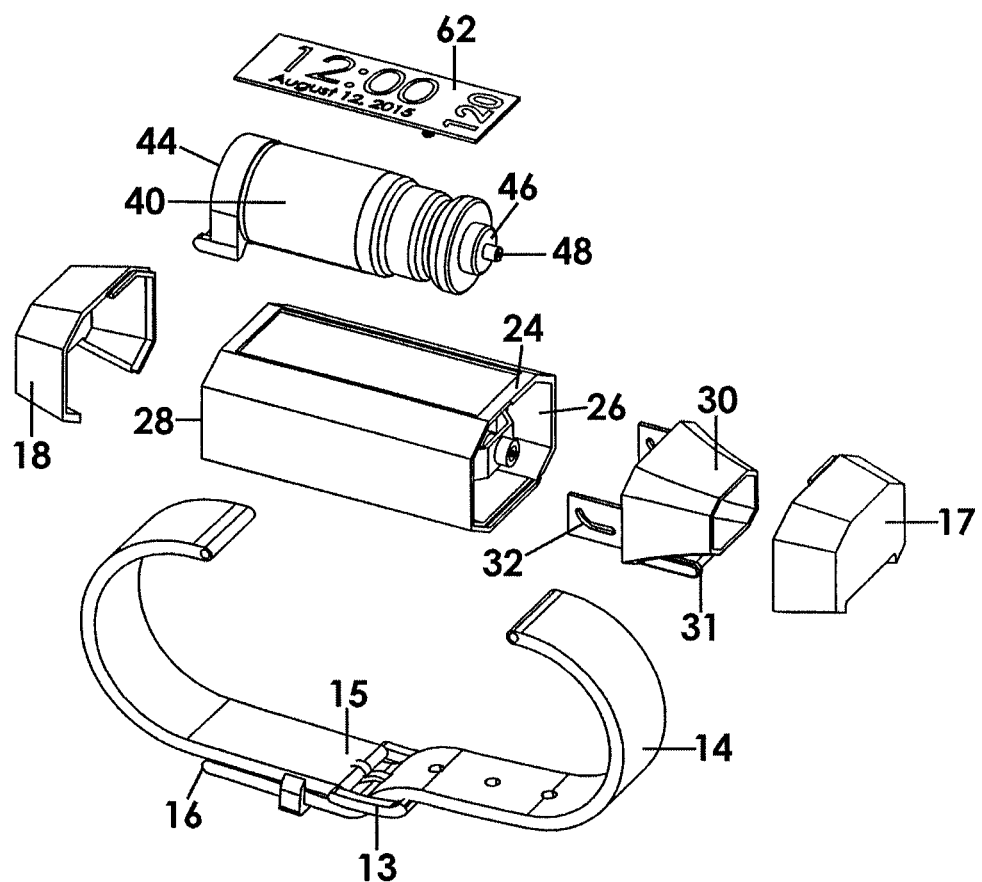

The dispensing assembly 160 includes a receiving spool 152 rotatably mounted in the base portion 122 of the housing 120. The receiving spool 152 may be in the form of an upstanding post defining a slot 154. A distal end 107 of the first layer 106 of the medicine strip once separated from the second layer 108 may be firmly but releasably coupled to the slot 154 of the receiving spool 152. The receiving spool 152 is operatively coupled to the index wheel 166 and to the lever 140 so as to rotate in coordination with the other rotatable components. A rotation of the receiving spool 152 causes the first layer 106 of the medicine strip 104 to be incrementally coiled about the receiving spool 152 (FIG. 10*b*). Similarly, a distal end 109 of the second layer 108 of the medicine strip 104 may be coupled to the contracting wheel 162 such that the second layer 108 is incrementally coiled about the fins 164 of the contracting wheel 162.

A separation member 134 is situated in the interior area of the base portion 122 adjacent the outlet port 128 and is configured to separate the first layer 106 from the second layer 108 as the layers are incrementally coiled around the receiving spool 152 and the contracting wheel 162, respectively. It is understood that the distal ends of the first and second layers of the medicine strip 104 may be initially coupled to the receiving spool 152 and contracting wheel 162 before the lever 140 is ever operated, i.e. when a new medicine strip 104 is loaded into the base portion 122.

The lever 140 is coupled to a shield 144 having a truncated annular configuration (i.e. like a portion of a ring). The shield 144 may be seen as concentrically adjacent the rim-shaped side wall 126. The shield 144 may be moved by operation of the lever 140 between an actuated configuration that blocks the outlet port 128 (FIG. 10*a*) and an unactuated configuration that does not block the outlet port 128. The lever 140 is coupled to a spring 142 and is configured such that the lever 140 is normally biased toward the unactuated configuration. However, when moved to an actuated configuration, the outlet port 128 is opened so that a respective individual medicine portion 110 may be delivered through the outlet port 128. An individual portion 110 of medicine is delivered into the dosage chamber 169 upon movement of the lever 140 to the actuated configuration (FIG. 10*b*). When a user slides the lever 140 to the unactuated configuration (FIG. 10*b*), the spring 142 is stretched but then automatically returns the lever 140 to the unactuated configuration when the user releases the lever 140. A timing wheel 150 (i.e. gear) is coupled to the lever 140 and operatively coupled to the index wheel 166, receiving spool 152, and the contracting wheel 162. Accordingly, movement of the lever 140 turns the timing wheel 150 which, in turn, operates the other respective wheels.

In use, the coordination of the wheel rotations consistently pulls the medicine strip 104 from its initial coiled configuration and feeds it toward the outlet port 128 where the layers are separated and the individual medicine portion is dispensed into the dosage chamber 169 and outlet port 128. Subsequent operations of the lever 140 repeat the dispensing process so long as there are undispensed individual medicine portions in the blister pack medicine strip 104. The medicine strip 104 may be removed by removing the lid portion 127 and removing the spent strip from the receiving spool 152 and contracting wheel 162.

A bottom surface of the base portion 122 of the housing 120 defines a dosage window 150 in visual communication into the interior area of the base portion 122. Correspondingly, a bottom surface of the timing wheel 150 includes a series of ordered numerical indicia 152 indicative of a number of doses of medicine that have been dispensed by respective actuations of said lever 140 or, alternatively, the number of doses remaining. Thus, a user can track how many times he has resorted to the inhaler for breathing assistance.

The watch assembly 60' is positioned atop the lid portion 127 of the housing 120 and has a construction substantially as described above. Namely, the watch assembly 60' may include a digital display 62', circuit board 64', and is energized by a battery 66'.

It is understood that while certain forms of this invention have been illustrated and described, it is not limited thereto except insofar as such limitations are included in the following claims and allowable functional equivalents thereof.

The invention claimed is:

1. A wearable wrist inhaler, comprising:
  a wristband having a first end and a second end configured for wear about a user's wrist;
  an inhaler unit releasably coupled to said wristband displaced from said first end and said second end, said inhaler unit including a housing having a plurality of walls defining an interior area and an outlet port in communication with the interior area;
  a watch assembly positioned atop said housing of said inhaler unit;
  a mouthpiece coupled to said outlet port of said housing;
  a medicine container containing a quantity of an inhaler medicament;
  a dispensing assembly in communication with said medicine container that is configured to dispense an individual portion of said medicament via said outlet port on demand by a user;
  wherein said dispensing assembly includes:
    an actuator nozzle mounted in said interior area of said housing and positioned adjacent to said outlet port of said housing;
    said medicine container includes a medicine canister situated in said interior area, said medical canister having a distal end accessible through an open rear end of said housing, an opposed proximal end, and a canister reservoir for holding a liquid medicine, said medicine canister having a valve stem extending from said opposed proximal end and nested in said actuator nozzle and being in fluid communication with said canister reservoir;
    wherein said medicine canister includes a spring-loaded actuator assembly operatively coupled to said valve stem and defining a channel between said canister reservoir and said valve stem, said channel being configured to block medicine from flowing from said canister reservoir to said valve stem when said actuator assembly is at a relaxed configuration and said channel being configured to allow medicine to flow from said canister reservoir to said valve stem when said actuator assembly is at a deployed configuration wherein said wristband includes a first cap member displaced from a second cap member, said housing being releasably coupled at a rear end to said first cap member, and releasably coupled to the outlet port to said second cap member.

2. The wearable wrist inhaler as in claim 1, wherein:
  said housing includes a bottom wall, an opposed top wall, and respective side walls extending between said top and bottom walls;

wherein said bottom wall, said opposed top wall, and said respective side walls of said housing define said interior area and said open rear end and said outlet port configured to provide access to said interior area;

said mouthpiece is in communication with said interior area, said mouthpiece being pivotally coupled to said housing adjacent said open front end and movable relative to said housing so as to adjust an angle of said mouthpiece relative to said housing.

3. The wearable wrist inhaler as in claim 1, wherein:
said spring-loaded actuator assembly includes a compression spring that normally biases said spring-loaded actuator assembly toward said relaxed configuration such that said channel is normally blocked;
said compression spring is compressed and said channel is unblocked when said distal end of said medicine canister is manually pushed into said interior area and said valve stem is correspondingly pushed firmly into said actuator nozzle.

4. The wearable wrist inhaler as in claim 3, wherein said channel is in fluid communication with a dosage chamber that permits only a predetermined amount of medicine from said canister reservoir to said valve stem when said actuator assembly is moved to said deployed configuration.

5. The wearable wrist inhaler as in claim 4, wherein said dosage chamber is filled with medicine from said canister reservoir via said channel when said spring-loaded actuator assembly is at said relaxed configuration and said dosage chamber is emptied into said valve stem when said spring-loaded actuator assembly is at said deployed configuration.

6. The wearable wrist inhaler as in claim 2, wherein:
said mouthpiece defines a guide slot having a arcuate configuration;
said housing includes a guide post proximate said outlet port to which said guide slot is pivotally coupled such that an angle of said mouthpiece is adjustable.

7. The wearable wrist inhaler as in claim 1, wherein said watch assembly includes:
a digital display positioned atop a top wall of said housing;
a circuit board configured to keep a current time by communicating with a world time server, said circuit board being in data communication with said digital display;
a battery electrically connected to said circuit board for energizing said circuit board and said digital display.

8. The wearable wrist inhaler as in claim 7, further comprising a dosage counter electrically connected to said circuit board and extending into an interior of said housing, said dosage counter positioned to be triggered by contact with said dispensing assembly each time said medicament is dispensed.

9. The wearable wrist inhaler as in claim 1, wherein said wristband includes a first clasp member displaced from a second clasp member, said housing being releasably coupled between said first clasp member and said second clasp member.

* * * * *